United States Patent [19]

Bussell et al.

[11] Patent Number: 5,759,168

[45] Date of Patent: Jun. 2, 1998

[54] SUPRAMALLEOLAR ANKLE FOOT ORTHOSIS

[76] Inventors: Mark H. Bussell, 6131 Curzon Ave., Apt. C, Ft. Worth, Tex. 76116; Thomas C. Lottermoser, P.O. Box 26, Revere Dr., Barrington, Ill. 60010

[21] Appl. No.: 277,503

[22] Filed: Jul. 19, 1994

Related U.S. Application Data

[63] Continuation of Ser. No. 781,359, Oct. 23, 1991, abandoned.

[51] Int. Cl.$^6$ ........................................ A61F 5/30
[52] U.S. Cl. ........................................ 602/27; 602/23
[58] Field of Search ........................... 602/27, 65, 23

[56] References Cited

U.S. PATENT DOCUMENTS

| | | | |
|---|---|---|---|
| 1,812,149 | 6/1931 | Hoggson | 602/65 |
| 3,955,565 | 5/1976 | Johnson, Jr. | |
| 4,280,489 | 7/1981 | Johnson, Jr. | |
| 4,554,912 | 11/1985 | Haberman | 602/27 |
| 4,556,054 | 12/1985 | Paulseth | 602/27 |
| 4,628,945 | 12/1986 | Johnson, Jr. | |
| 4,638,794 | 1/1987 | Grisar | 602/27 |
| 4,729,370 | 3/1988 | Kallassy | |
| 4,821,743 | 4/1989 | Wetz | 36/89 |
| 4,844,094 | 7/1989 | Grim | |
| 4,934,355 | 6/1990 | Porcelli | 602/27 |
| 4,938,777 | 7/1990 | Mason et al. | 602/27 |
| 4,964,402 | 10/1990 | Grim et al. | 602/27 |

FOREIGN PATENT DOCUMENTS

| | | | |
|---|---|---|---|
| 3916091 | 11/1990 | Germany | 602/27 |
| 8201659 | 5/1982 | WIPO | 602/27 |

OTHER PUBLICATIONS

Roylan advertisement, source unknown, publication date unknown.

Donjoy advertisement, source unknown, publication date unknown.

Kallassy advertisement, source unknown, publication date unknown.

Swede–O–Universal advertisement, published by Professional Medical Products, Inc., publication date unknown.

Trueform advertisement, source unknown, publication date unknown, pp. I–33, 34, and 37.

Ligamentus Ankle Support, published by United States Manufacturing Co., publication date unknown.

Stover, C.N., "Functional Management of a Sprained Ankle with an Air–Stirrup Ankle Brace," published by Aircast, Inc., publication date unknown.

Air–Stirrup Ankle Brace Advertisement, published by Aircast, Inc. publication date unknown.

Gel Ankle Brace advertisement, source unknown, publication date unknown.

Pending U.S. Patent Application Serial No. 08/467,732, Filed On Jun. 6, 1995, Inventor: Bussell et al.

Bussell, Mark H., et al., "Innovative Design in a Supramalleolar Ankle Foot Orthosis," 1990 Congress/Academy Abstracts, Arch Phys Med Rehabil, vol. 71, No. 10, Sep., 1990, p. 807.

*Primary Examiner*—Lynne A. Reichard
*Attorney, Agent, or Firm*—Brinks Hofer Gilson & Lione

[57] ABSTRACT

An ankle brace which includes an inverted "Y" joint located at the malleoli of the ankle. The ankle brace is formed into the shape of the patient's ankle and then sections of the brace are cut out to form the present invention. In particular, an inverted "Y" joint is manufactured by cutting out a delta-shaped opening.

39 Claims, 5 Drawing Sheets

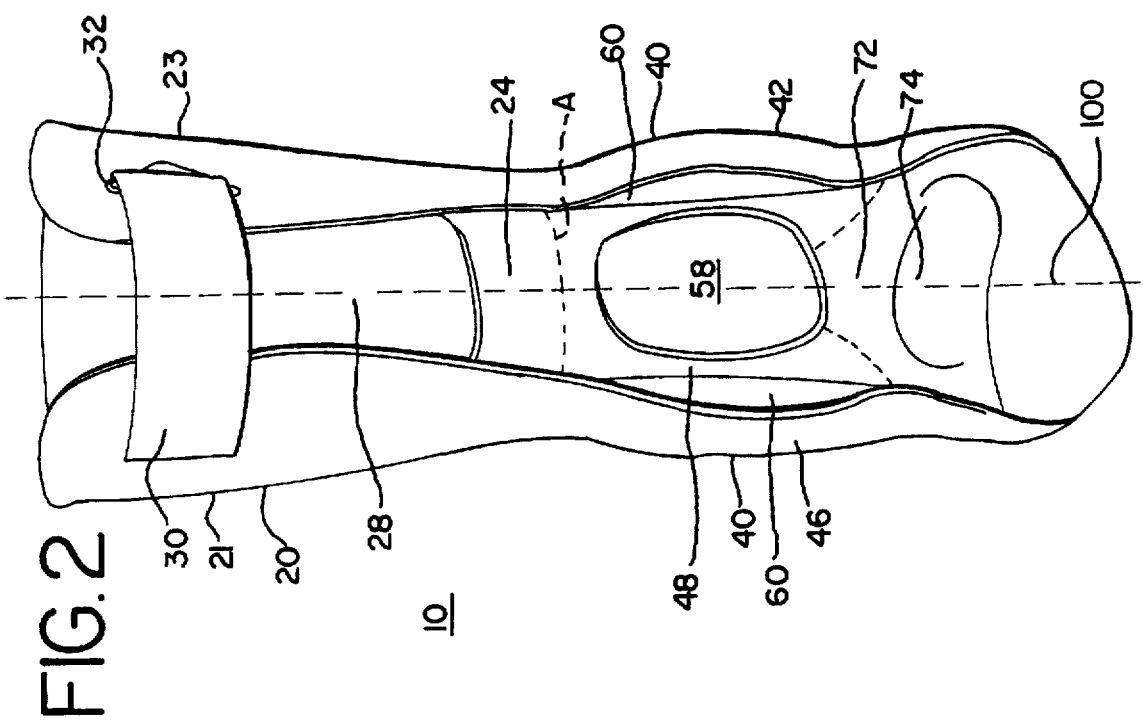
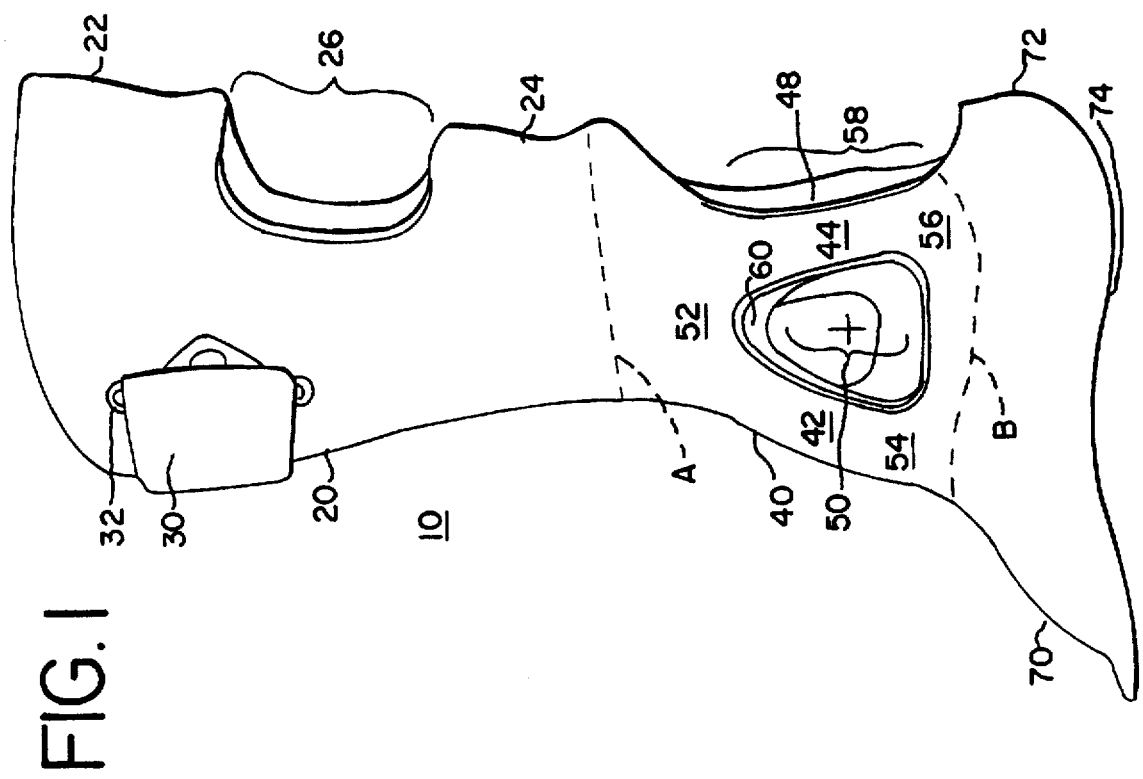

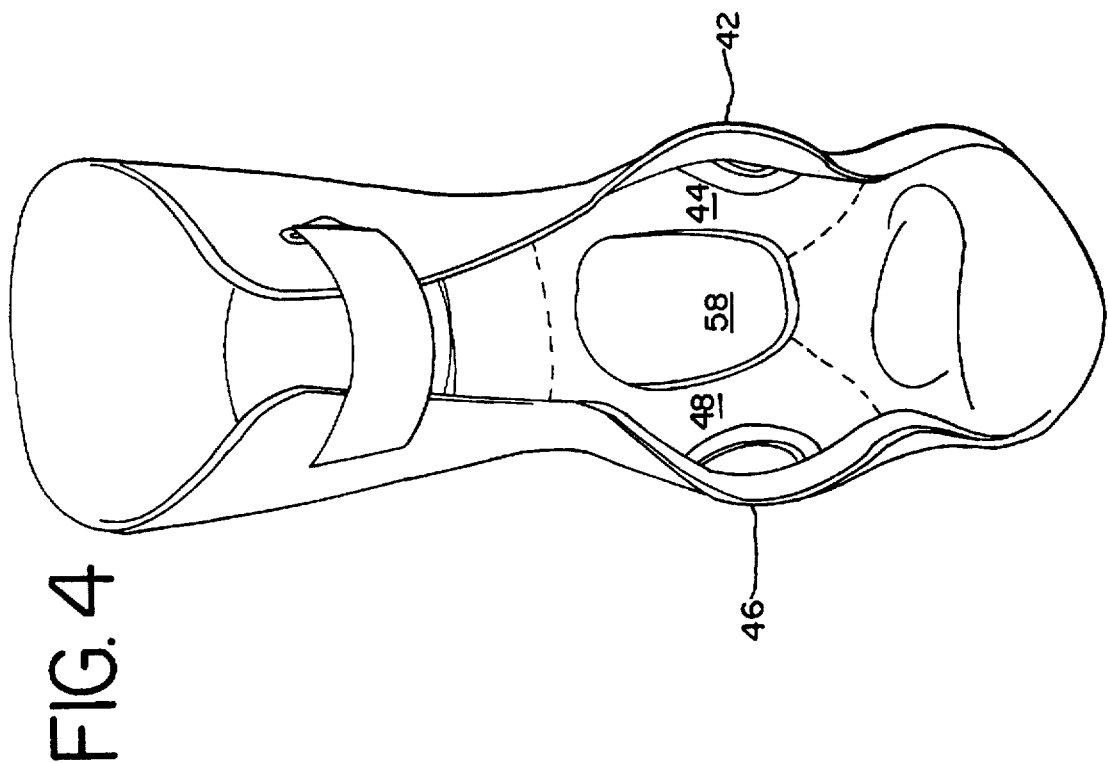
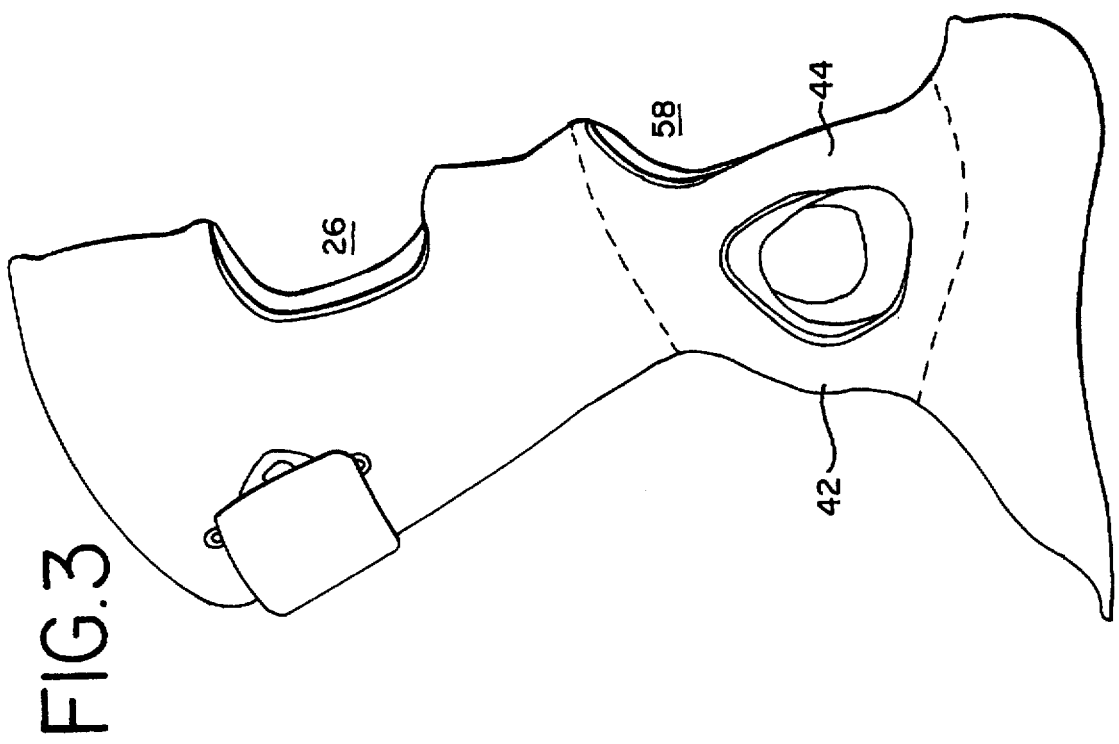

SUPRAMALLEOLAR ANKLE FOOT ORTHOSIS

This application is a continuation of application Ser. No. 07/781,359, filed Oct. 23, 1991 now abandoned.

FIELD OF THE INVENTION

Inversion ankle sprain is a frequently encountered athletic injury which most commonly involves the anterior talofibular ligament. A variety of treatment modalities have evolved to minimize inflammation, restore motion and agility, and prevent reinjury. Grade I, II, and III ankle sprains are best treated by early mobilization. This rehabilitation has commonly included the utilization of a commercially available ankle support that allows flexion (dorsiflexion) and extension (plan-tarflexion) while restricting other motion.

The present invention is an alternative to other prefabricated ankle supports. In the present invention, an innovative inverted "Y" ankle joint design allows unrestricted plantar flexion and dorsiflexion yet virtually eliminates ankle inversion and eversion. The present invention incorporates a one piece padded inverted "Y" polyethylene ankle joint which intimately cradles both malleoli. The applications for the present invention include chronic recurrent inversion sprains, painful subtalar motion, and prophylaxis in high risk groups.

The intimate fit and the superior mediolateral stability make the present invention unique and superior to any other commercially available ankle supports.

BACKGROUND OF THE INVENTION

The present invention was developed in response to the growing needs of patients with medial and lateral ankle instability, most being inversion or lateral anterior talofibular ligament laxity. The anterior talofibular ligament is the most commonly torn ligament in the human body.

Traditional treatment for inversion ankle injuries includes reduction of edema, restoration of motion, muscle strengthening, and prevention of reinjury. The present invention is unique in that it can be used both in the rehabilitation period and for prophylaxis of reinjury. The most significant aspect of the invention is the flexible one piece plastic inverted "Y" ankle joint attached to a plastic heel cup. The development of this invention was brought about through frustration with the ineffective immobilization of subtalar motion with other commercially available ankle braces and supports.

The present invention offers far superior subtalar control of inversion and eversion at the ankle. It is unique in that it is a flexible one piece design. It has been successfully used on a number of patients with serious ankle ligament tears. It has long been desired to have a device that immobilizes the subtalar inversion and eversion at the ankle joint yet allows free dorsiflexion and plantar flexion.

The least effective form of immobilization is seen in soft ankle garments such as those under the trade names Roylan Ankle Wrap (Spandex) and the Donjoy Neoprene Ankle Supports. The support device under the tradename Donjoy Ankle Ligament Protector is a thermoplastic heel cup that articulates with a supramalleolar ankle strap.

The axis of ankle motion is posterior and superior to the actual axis of ankle flexion and extension. The device under the tradename Kallassy Ankle Support is another neoprene support utilizing medial and lateral stabilizing straps. (U.S. Pat. No. 4,729,370) The support device under the tradename Swede-o-Universal ankle support is canvas and elastic with plastic and metal supports but no ankle joint. All of the above listed devices afford extremely limited control of inversion and eversion. Due to the elastic nature of the aforementioned prior art, inversion and eversion at the ankle is merely restricted yet not truly controlled as is in the present invention.

U.S. Pat. No. 3,955,565 describes a relatively rigid immobilization of the limb when applied to an ankle joint. This allows for adapting to various circumferences and anatomy of the ankle joint, although it does not allow for unrestricted plantar flexion and dorsiflexion as does the present invention.

The most commercially successful ankle brace used to control inversion and eversion of the ankle joint is the walking cast commercially available under the trademark AIRCAST as described in U.S. Pat. Nos. 4,280,489 and 4,628,945. These devices consist of two separate medial and lateral panels connected by a flexible U-shaped stirrup. Due to the nature of the flexible U-shaped stirrup, the panels are allowed to move freely with respect to one another. Because of the ease of movement between the medial and lateral panels there is a lack of control of inversion and eversion. Also, in the AIRCAST products, lack of control of inversion and eversion is also due to the lack of a heel cup attached to the medial and lateral panels as in the present invention. Lastly, the joint axis of the AIRCAST products is inferior to the panels at the junction of the U-shaped stirrup. This joint axis on the aforementioned prior art is inferior to the anatomical joint axis of the ankle joint. Because of this there is migration of the AIRCAST on plantar flexion and dorsiflexion. In the present invention, the joint axis is in close proximity to the anatomical axis of the ankle joint and thus less migration is afforded in the plantar flexion and dorsiflexion. Another ankle brace described by U.S. Pat. No. 4,844,094 improves upon the deficiencies in the ankle brace described by U.S. Pat. Nos. 4,280,489 and 4,628,945.

U.S. Pat. No. 4,844,094 attempts to overcome deficiencies present in U.S. Pat. No. 4,280,489 by replacing the air cushion bladders with a gel material and also by adding an attachment whereas the medial and lateral panels are directly laced to the shoe. Although control of inversion and eversion is improved, the same basic deficiencies as seen in the AIRCAST products are still seen.

The next class of devices of interest is rigid plastic monocentric ankle joint braces such as the devices under the tradenames 3D Ankle Orthosis, Ligamentus Ankle support and STA-Bil Ankle Brace. These are all made of rigid plastic and provide increased medial lateral stability, but lack comfort secondary to their rigid nature and the nonanatomic monocentric ankle joint.

The competitive and noncompetitive athletes who sustain anterior talofibular ligament and other ligamentous injuries to the ankle demand early return to activity and prevention of reinjury. In these athletes, the present invention achieves a level of subtalar immobilization unequaled by the plethora of commercially available ankle supports and braces, while allowing unrestricted dorsiflexion and plantarflexion.

DETAILED DESCRIPTION OF DRAWINGS

FIG. 1 is a lateral or side view of an embodiment of the present invention in an unflexed or neutral position;

FIG. 2 is a front or anterior view of the embodiment of FIG. 1;

FIG. 3 is a side view of the embodiment of FIG. 1 in a dorsiflexion position;

FIG. 4 is an anterior view of the embodiment of FIG. 3;

SUMMARY OF THE INVENTION

Figure 6:
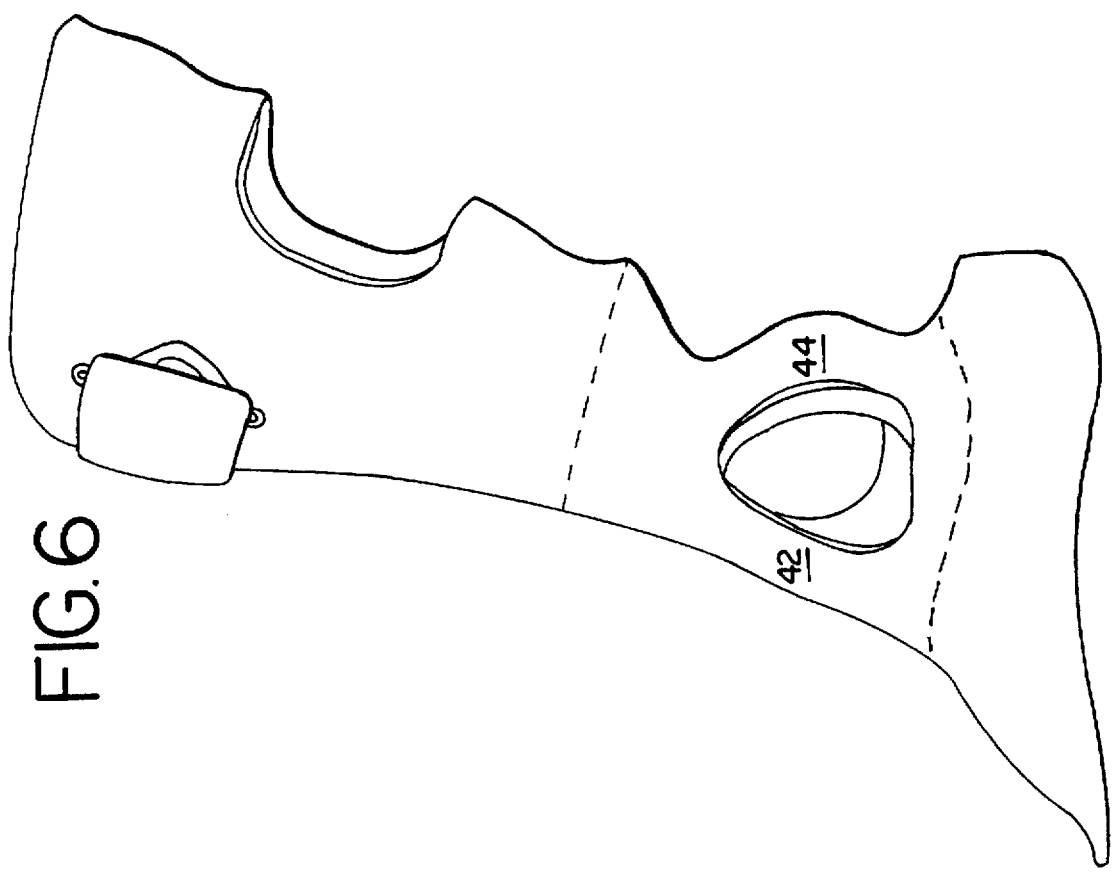
FIG. 6 is a side view of the embodiment of FIG. 1 in a plantar flexion position.

The present invention is directed to an ankle brace which has a shape identical to a person's ankle and which has an inverted "Y" joint positioned at the malleoli. The invention provides significantly improved medial/lateral, inversion/ eversion control of the subtalar ankle motion over any other commercially available ankle orthosis, while allowing unrestricted dorsiflexion and plantar flexion.

The one piece flexible inverted "Y" ankle joint allows a polycentric ankle motion in dorsiflexion and plantar flexion that conforms to the anatomical axis of ankle joint motion.

The present invention has improved control of the calcaneous secondary to a heel cup being attached to the flexible inverted "Y" joint.

The present invention provides increased comfort secondary to the flexible nature of the plastic allowing greater conformation to the patient's anatomy of the ankle while the tensile strength of the polyethylene provides superior resistance to inversion and eversion.

The one piece design results in a decrease in fabrication time and decreased production costs of assembly.

The present invention improves healing and decreases recovery time in severe ankle sprains secondary to the improved medial lateral stability while allowing free range of motion in dorsiflexion and plantar flexion during the recovery process.

DETAILED DESCRIPTION OF PREFERRED EMBODIMENT

The present invention is best understood upon viewing a preferred embodiment illustrated in FIGS. 1-7.

In FIG. 1 a lateral view of one preferred embodiment of a left foot model of the ankle brace 10 is shown in a neutral or unflexed state. The ankle brace 10 is made of a single piece of flexible material such as polyethylene having a thickness ranging from about 1/16 of an inch to 3/16 of an inch. As described below, the single piece of material is initially formed into a shape identical to the exterior surface of the calf, ankle, and foot of a patient. The final manufactured product comprises an upper section 20 to support the calf. The upper section 20 consists of a medial panel 21 and a lateral panel 23. Upper section 20 extends from the top of the ankle brace 10 to the superior margin line A indicated by the dashed lines. Superior margin line A is located 1" to 1½" above the apex of the malleoli of the ankle. As will be described, the superior margin A represents where the padding material, such as the material sold under the trademark of ALIPLAST, tapers to a zero thickness in the middle section of the ankle brace 10. Upper section 20 comprises a proximal posterior band 22 and a middle posterior band 24. There is a posterior superior opening 26 located between proximal and middle posterior bands 22 and 24. Posterior superior opening 26 has a width of about 2" to 2½" and a height of about 2" to 2½". The bottom of the posterior superior opening is located approximately 5" to 6" above the ground. The proximal posterior band 22 and middle posterior band 24 are important in limiting the vertical movement between the medial panel 21 and the lateral panel 23 of the brace. Thus, the amount of vertical shear movement between the brace and the leg is minimized.

From the anterior view of FIG. 2, the upper section 20 has a longitudinal-like opening 28 extending along the length of the ankle brace 10 and a vertical sagittal plane 100 (schematically shown by dashed lines in FIG. 2) defined to approximately bisect the ankle and foot when inserted in the ankle brace 10. When the ankle brace 10 is worn, a tight fit is insured by employing an attachment device to attach those sections of the upper section 20 on opposite sides of the longitudinal-like opening 28. The attachment device may consist of a proximal anterior strap 30 made of a loop attachment material, such as the material sold under the trademark of VELCRO, and attached to one side of the longitudinal-like opening 28. The strap 30 is then threaded through a loop 32 attached to the other side of the longitudinal-like opening 28.

Below the upper section 20 is a middle section 40 which is integrally connected to upper section 20. As seen in FIGS. 1 and 2, the middle section 40 comprises inverted "Y" joints at the lateral and medial sides of the ankle brace 10. In particular, the inverted "Y" joint on the lateral side has a lateral anterior strut 42 and a lateral posterior strut 44. On the medial side of the ankle brace 10 the inverted "Y" joint has a medial anterior strut 46 and a medial posterior strut 48. Each of the struts 42, 44, 46, and 48 has a width of approximately ½ inch. Each inverted "Y" joint has a Delta-shaped opening 50 marked by a crossmark which indicates the position of the apex of the lateral malleolus in FIG. 1. The three corners of the Delta-shaped opening 50 are denoted by numerals 52, 54, and 56. Top corner 52 has an approximate angle of 40 degrees. Bottom corners 54 and 56 each have an approximate angle of 70 degrees. The center of the medial Delta-shaped opening is approximately ½ to ¾ of an inch anterior and superior to the center of the lateral Delta-shaped opening.

The middle section 40 further includes a posterior inferior opening 58 which is bounded by posterior struts 44 and 48. The posterior inferior opening 58 has a width of about 2" to 2½" and a height of about 2½" to 3". The bottom of the posterior inferior opening is located approximately 1" to 1½" above the ground. The middle section 40 includes a padding material 60 consisting of a foam material, such as the material sold under the trademark of ALIPLAST, and having a thickness of approximately ½". The padding material is attached to the inside surface of the middle section by adhesive glue. The thickness of the padding material is tapered to zero at the superior margin line A and inferior margin line B.

Inferior margin line B indicates the demarcation between the middle section 40 and a bottom section 70 which provides support to the patient's foot. Inferior margin line B is located 1" to 1½" below the apex of the malleoli of the ankle. Bottom section 70 has a heel cup 72 and a plantar surface 74. Heel cup 72 provides support for the patient's heel and plantar surface 74 provides support for the sole of a patient's foot.

The above described embodiment of the invention may be prefabricated in approximately twelve sizes including six for the right ankle and six for the left ankle. Each size will have a small, medium and large all with regular and wide sizes. The height of the preferred embodiment is approximately 10" in the average adult model, although a shorter version of approximately 6 inches can be fabricated by trimming to the level of the middle posterior band 24 in FIG. 1. The length of the plantar surface 74 is approximately 4–5 inches.

Fabrication of this invention requires a positive Plaster-of-Paris model of the foot and ankle. Placement of approximately ½" foam material interface, wherein the foam material interface is made of a material such as the material sold under the trademark of ALIPLAST, over the apex of both the medial and lateral malleoli is utilized. This foam material interface is attached directly to the positive model, prior to vacuum forming heated polyethylene over the model. This foam material interface is tapered to zero thickness approximately 1" to 1½" proximal and distal to the apex of the malleoli. This provides relief areas for any bony prominences around the ankle. In addition to providing relief, the convex shaping produced by the tapering of the foam material interface forms a radius of curvature which allows the anterior and posterior struts of the inverted "Y" joint to bow away from the ankle in both plantar flexion and dorsiflexion. There are two different curvatures formed both in the vertical or coronal plane and the horizontal or transverse plane. The curvature in the vertical or coronal plane of the anterior and posterior struts of the inverted "Y" joint has a radius of curvature of approximately 4 inches. In the horizontal or transverse plane, the radius of curvature is much larger with a radius of approximately 12" in the average adult model. After the foam material is shaped over the ankle area, a sheet of 3/16" polyethylene is heated in an oven and vacuum formed with suction over the positive model of the foot and ankle.

After the plastic cools, the positive model is removed and the various openings previously mentioned are cut out of the plastic to form the final product.

The radius of curvature in both the horizontal and vertical planes may be achieved by directly modifying the positive model without using foam material. Instead of foam materials, such as the material known under the trademark of ALIPLAST, cushions such as an air bladder or gel bladder such as described in U.S. Pat. Nos. 4,628,945 and 4,844,094, respectively, could then be used as a comfortable interface between the polyethylene and the leg.

Positioning of the inverted "Y" ankle joint is over the apex of the medial and lateral malleoli insuring that the mechanical joint axis of the invention simulates the anatomical axis of the ankle joint. The center of the inverted "Y" joint leaves an opening which is a modified delta shape which has rounded corners. The angles of the delta shape are as follows: the superior angle is approximately 40° in the average adult model and the inferior angles are approximately 70°. The center of the delta shape is placed precisely over the apex of the malleoli. This positioning places the anterior struts of the inverted "Y" ankle joint along the same course of path as the lateral anterior talofibular ligament and the medial deltoid ligament of the ankle. The size of the delta shape formed by the inverted "Y" ankle joint will vary according to the size of the model. The vertical length will be approximately from 1½" to 2" and the horizontal length will be approximately from 1" to 1½".

Figure 5:
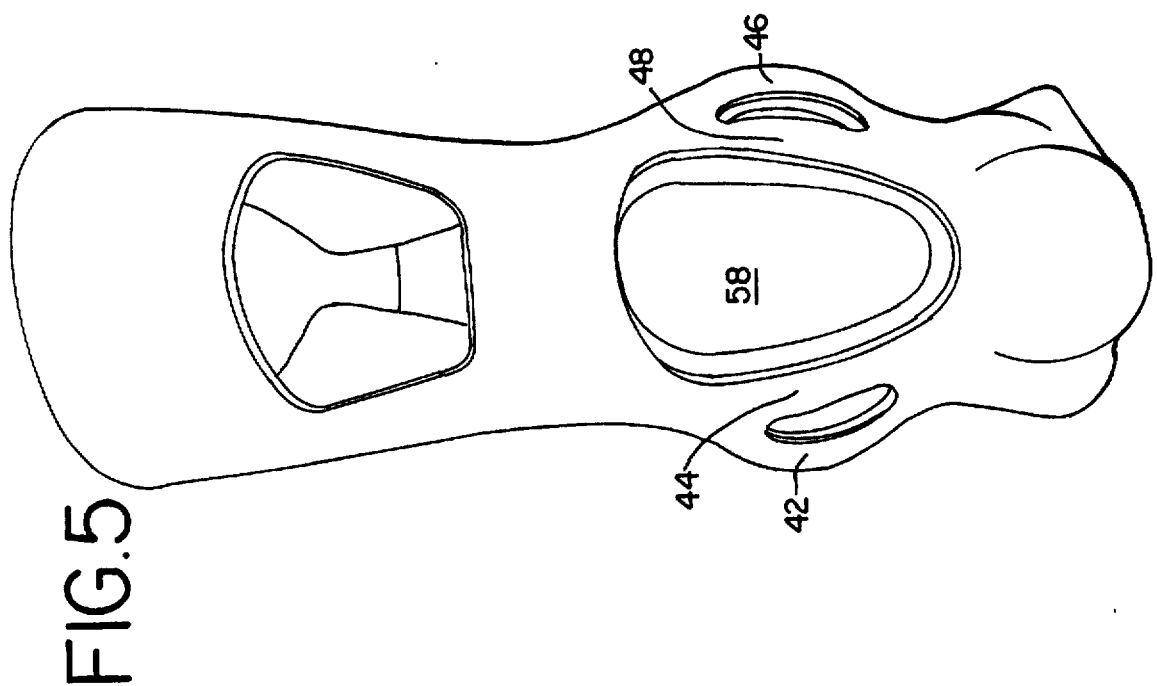
FIG. 5 is a posterior view of the embodiment of FIG. 3.

The above description describes the manufacture and structure of the preferred embodiment of the ankle brace in a neutral or unflexed state. As seen in FIGS. 3–5, when the ankle undergoes dorsiflexion the anterior struts 42 and 46 both bulge away from the midline of the ankle. The radius of curvature of anterior struts 42 and 46 in the vertical or coronal plane decreases with increasing dorsiflexion. Also, the posterior struts 44 and 48 become taut and the posterior inferior opening 58 becomes narrower at its inferior margin during dorsiflexion. By becoming taut, posterior struts 44 and 48 limit inversion and eversion of the heel cup. Furthermore, the radius of curvature of the struts 42, 44, 46, and 48 increases in the transverse or horizontal plane during dorsiflexion.

As illustrated in FIGS. 5 and 6, plantar flexion of the preferred embodiment of the invention results in struts 44 and 48 bulging away from the midline of the ankle. The radius of curvature in the vertical or coronal plane of struts 44 and 48 decreases with further plantar flexion and struts 42 and 46 simultaneously become taut and closer together. Similarly, by becoming taut on plantar flexion, struts 42 and 46 limit inversion and eversion of the heel cup.

Figure 8:
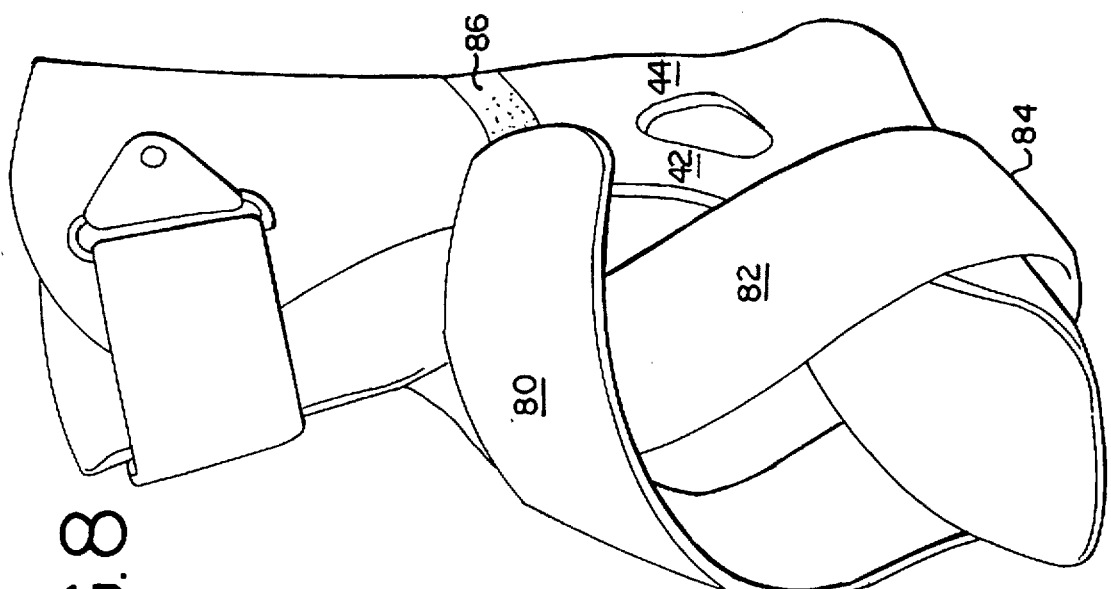
FIG. 8 is a lateral oblique view of another embodiment with optional inversion and eversion straps.
Figure 7:
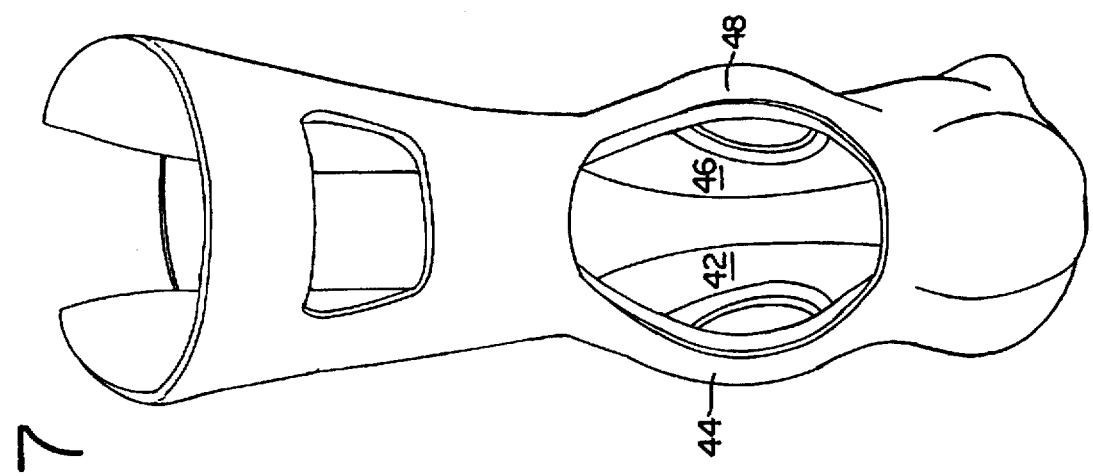
FIG. 7 is a posterior or back view of the embodiment of FIG. 6.

In another embodiment of the present invention illustrated in FIG. 8, eversion strap 80 and inversion strap 82 may be employed to provide a more secure fit between the ankle and the ankle brace 10. Straps 80 and 82 are formed of a single strap 84 preferably made of the material sold under the tradename VEL-FOAM. The single strap 84 is attached to the bottom of the plantar section 74 by a strip of adhesive material preferably sold under the tradename VELCRO. The adhesive strip has a hook located on the bottom of the plantar section 74.

The strap 84 is then crossed over itself to define the eversion strap 80 and inversion strap 82. Eversion strap 80 is preferably attached to an adhesive Velcro hook attachment 86 located approximate to the middle posterior band 24 on the lateral side. The inversion strap 82 is attached in a similar manner to the middle posterior band 24 on the medial side. This embodiment achieves greater confirmation of the orthosis to the ankle, although a snug fit in a shoe normally allows adequate confirmation.

Figure 9:
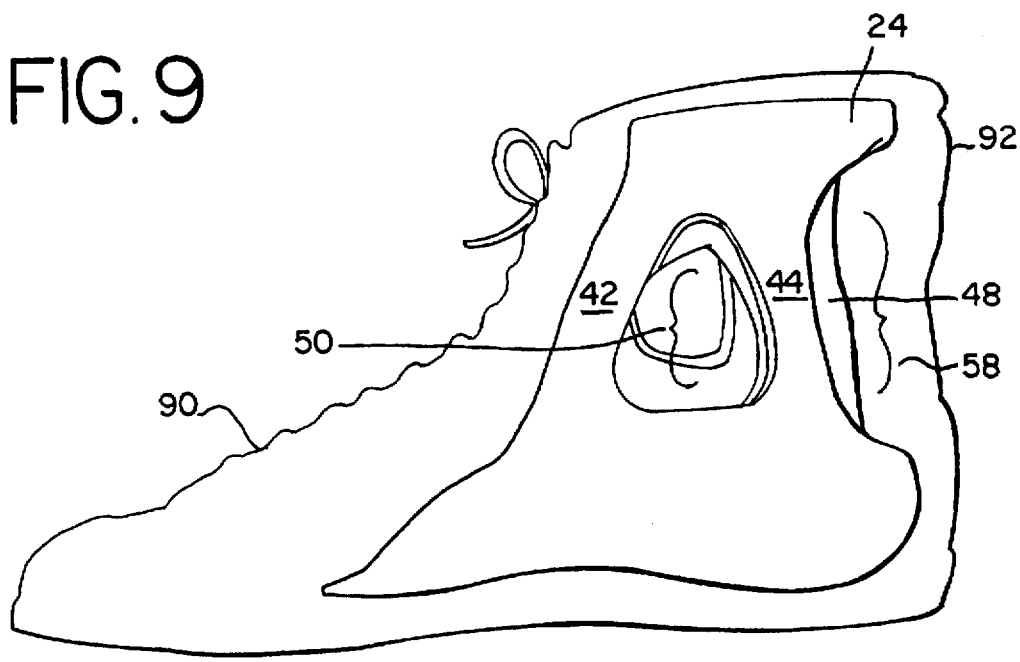
FIG. 9 is a lateral view of an embodiment of the present invention inside of a gym shoe.
Figure 10:
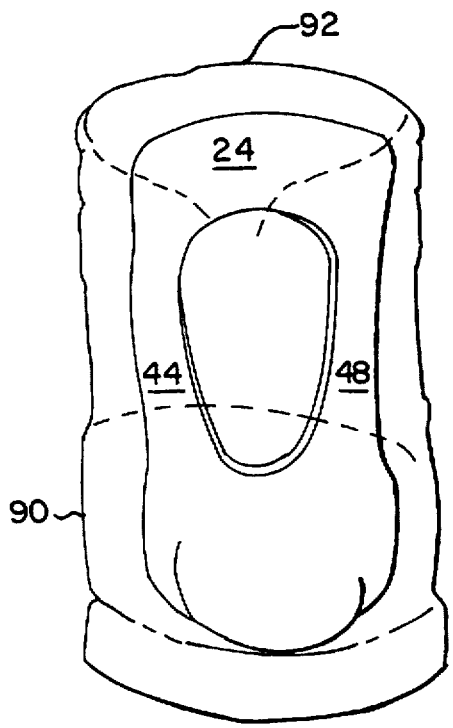
FIG. 10 is a posterior view of the embodiment of FIG. 9.
Figure 11:
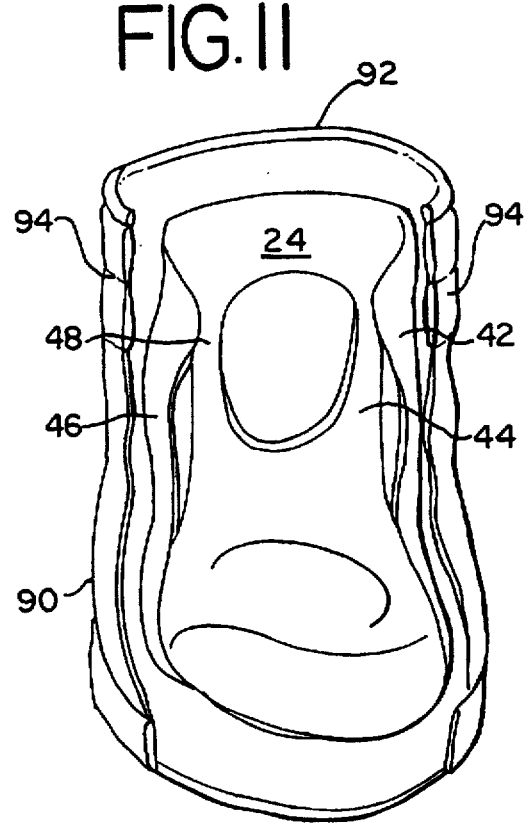
FIG. 11 is an anterior cut away view of the embodiment of FIG. 9.

In FIGS. 9–11 another embodiment of the present invention is shown. Specifically, the embodiment of FIGS. 9–11 involves the ankle brace described previously incorporated in a shoe, preferably a high top gym or football shoe 90. As seen in FIG. 9, the ankle brace 10 is shortened so that the middle posterior band 24 is near the posterior or back wall 92 of the shoe 90. For visualization purposes only, the sidewalls 94 of the shoe 90 are separated from the ankle brace 10, but in fact the ankle brace 10 is incorporated in the walls of the shoe 90. Incorporation is accomplished by fabricating the flexible polyethylene ankle brace into the outer shell of the shoe and the inner padding 60 could be incorporated into the lining of the shoe 90 as seen in FIGS. 9–11.

While the invention has been described with relation to certain presently preferred embodiments, those with skill in this art will recognize other modifications of the invention which will still fall within the scope of the invention, as expressed in the accompanying claims. For example, the invention may be applied to other joints such as a knee or elbow.

We claim:

1. An ankle brace to be worn on an ankle and foot of a person comprising:
   a single unitary surface having a pre-worn shape that is adapted to conform to an exterior surface of said ankle and foot, wherein said surface with said pre-worn shape comprises:
   (a) an upper section to support the calf of the person, (b) a middle section integrally connected to said upper section and comprising a flexible and inverted "Y" joint to support the ankle of the person, wherein said inverted "Y" joint forms an opening, wherein said opening is adapted to be aligned with the malleoli of the person, and (c) a bottom section supporting the foot of the person and integrally connected to said middle section, wherein said inverted "Y" joint permanently supports said upper section at a fixed predetermined position above said bottom section and is configured so as to allow unrestricted plantar flexion and dorsiflexion.

2. The ankle brace of claim 1, wherein said upper section, said middle section, and said bottom section each comprise a flexible material.

3. The ankle brace of claim 1, wherein said opening is Delta-shaped and has three corners.

4. The ankle brace of claim 3, wherein the angles of the three corners are approximately 40 degrees, 70 degrees, and 70 degrees.

5. The ankle brace of claim 1, further comprising a heel cup connected to the inverted "Y" joint.

6. The ankle brace of claim 1, wherein said middle section possesses a first radius of curvature in a horizontal plane and a second radius of curvature in a vertical plane.

7. The ankle brace of claim 1, further comprising a padding material attached to the inside surface of either the upper, middle, or bottom section.

8. The ankle brace of claim 7, wherein said padding material is attached to the inside surface of the middle section.

9. The ankle brace of claim 7, wherein the padding material is made of a foam material.

10. The ankle brace of claim 7, wherein the padding material is made of either an air bladder or a gel bladder.

11. The ankle brace of claim 1, wherein said single unitary surface comprises a single material.

12. The ankle brace of claim 1, wherein said middle section comprises a second inverted "Y" joint to support the ankle of the person.

13. The ankle brace of claim 1, wherein said opening does not intersect a sagittal plane defined by said ankle and foot.

14. The ankle brace of claim 1, wherein said inverted "Y" joint defines two downwardly pointing arms which are both integrally connected to said bottom section.

15. An ankle brace to be worn on an ankle and foot of a person comprising:

a continuous surface made of a single material and having a substantially pre-worn shape that is adapted to conform to an exterior surface of said ankle and foot, said continuous surface with said pre-worn shape comprising:

(a) an upper section to support the calf of the person, (b) a middle section integrally connected to said upper section and comprising a flexible and inverted "Y" joint to support the ankle of the person wherein said inverted "Y" joint forms an opening, wherein said opening is adapted to be aligned with the malleoli of the person, and (c) a bottom section integrally connected to said middle section and supporting the foot of the person, wherein said "Y" joint is configured so as to allow unrestricted plantar flexion and dorsiflexion.

16. The ankle brace of claim 15, wherein said upper section is integrally connected to said middle section, and said bottom section is integrally connected to said middle section.

17. The ankle brace of claim 15, wherein said "Y" joint defines a Delta-shaped opening having three corners.

18. The ankle brace of claim 17, wherein the angles of the three corners are approximately 40 degrees, 70 degrees, and 70 degrees.

19. The ankle brace of claim 15, further comprising a heel cup connected to the inverted "Y" joint.

20. The ankle brace of claim 15, wherein said middle section possesses a first radius of curvature in a horizontal plane and a second radius of curvature in a vertical plane.

21. The ankle brace of claim 15, further comprising a padding material attached to the inside surface of either the upper, middle, or bottom section.

22. The ankle brace of claim 21, wherein said padding material is attached to the inside surface of the middle section.

23. The ankle brace of claim 22, wherein the padding material is made of a foam material.

24. The ankle brace of claim 22, wherein the padding material is made of either an air bladder or a gel bladder.

25. The ankle brace of claim 15, wherein said middle section comprises a second inverted "Y" joint to support the ankle of the person.

26. The ankle brace of claim 15, wherein said opening does not intersect a sagittal plane defined by said ankle and foot.

27. The ankle brace of claim 15, wherein said inverted "Y" joint defines two downwardly pointing arms which are both integrally connected to said bottom section.

28. An ankle brace to be worn on an ankle and foot of a person comprising:

an upper section to support the calf of the person, a middle section integrally connected to said upper section and comprising a first flexible and inverted "Y" joint and a second flexible "Y" joint to support the ankle of the person, and a bottom section integrally connected to said middle section and supporting the foot of the person, wherein said first and second "Y" joints are configured so as to allow unrestricted plantar flexion and dorsiflexion, wherein said upper, middle and bottom sections having a combined pre-worn shape that is adapted to conform to an exterior surface of said ankle and foot.

29. The ankle brace of claim 28, wherein said upper section is integrally connected to said middle section, and said bottom section is integrally connected to said middle section.

30. The ankle brace of claim 28, wherein said first "Y" joint defines a Delta-shaped opening having three corners.

31. The ankle brace of claim 30, wherein the angles of the three corners are approximately 40 degrees, 70 degrees, and 70 degrees.

32. The ankle brace of claim 28, further comprising a heel cup connected to the first inverted "Y" joint and said second inverted "Y" joint.

33. The ankle brace of claim 28, wherein said middle section possesses a first radius of curvature in a horizontal plane and a second radius of curvature in a vertical plane.

34. The ankle brace of claim 28, further comprising a padding material attached to the inside surface of either the upper, middle, or bottom section.

35. The ankle brace of claim 34, wherein said padding material is attached to the inside surface of the middle section.

36. The ankle brace of claim 34, wherein the padding material is made of a foam material.

37. The ankle brace of claim 34, wherein the padding material is made of either an air bladder or a gel bladder.

38. The ankle brace of claim 30, wherein said Delta-shaped opening does not intersect a sagittal plane defined by said ankle and foot.

39. The ankle brace of claim 28, wherein said first inverted "Y" joint defines two downwardly pointing arms which are both integrally connected to said bottom section.

* * * * *